United States Patent
Kokubu

(12) 
(10) Patent No.: US 6,179,830 B1
(45) Date of Patent: Jan. 30, 2001

(54) LASER PROBE

(75) Inventor: Shinji Kokubu, Sendai (JP)

(73) Assignee: J. Morita Manufacturing Corporation, Kyoto (JP)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/898,143

(22) Filed: Jul. 22, 1997

(30) Foreign Application Priority Data

Jul. 24, 1996 (JP) .................................................. 8-212134

(51) Int. Cl.[7] .................................................. A61B 18/18
(52) U.S. Cl. .................................. 606/16; 606/15; 606/2; 607/93; 433/215; 385/124; 385/126
(58) Field of Search ........................... 606/2, 3, 9, 13, 606/15, 16; 607/89, 93; 385/142, 126, 123, 124; 250/493.1; 433/29–31, 215

(56) References Cited

U.S. PATENT DOCUMENTS

| | | | |
|---|---|---|---|
| 4,273,109 | * | 6/1981 | Enderby .................................. 606/16 |
| 4,435,040 | * | 3/1984 | Cohen et al. . | |
| 4,852,968 | * | 8/1989 | Reed . | |
| 5,013,131 | * | 5/1991 | Fotheringham . | |
| 5,364,391 | * | 11/1994 | Konwitz .................................. 606/13 |
| 5,491,767 | * | 2/1996 | McPherson et al. ................... 606/16 |
| 5,557,701 | * | 9/1996 | Krivoshlykov et al. ............. 385/124 |
| 5,659,649 | * | 8/1997 | Nouchi et al. ........................ 385/124 |
| 5,738,677 | * | 4/1998 | Colvard et al. ........................... 606/2 |

FOREIGN PATENT DOCUMENTS

| | | |
|---|---|---|
| 3444824 | 6/1986 | (DE) . |
| 3717142 | 6/1988 | (DE) . |
| 195 38 990 | 10/1995 | (DE) . |
| 2-297986 | 12/1990 | (JP) . |
| WO85/05350 | 12/1985 | (WO) . |

* cited by examiner

*Primary Examiner*—Linda C. M. Dvorak
*Assistant Examiner*—Bryan K. Yarnell
(74) *Attorney, Agent, or Firm*—Koda & Androlia

(57) ABSTRACT

In evaporation of an organic hard tissue, a damage of a light emitting face of an optical fiber composing a laser probe is suppressed. A laser light source 13 outputs pulsate laser light of a wavelength of 1.0 $\mu$m to 5.5 $\mu$m and an output energy of 1 mJ to 2,500 mJ. The laser light is guided to a contact type handpiece 15 via a waveguide 14. The operator makes a light emitting face 17 of an optical fiber 9 of a probe 16 which is detachably attached to the tip end of the handpiece 15 contact with the surface of an organic hard tissue. In the optical fiber 9, an intermediate layer exists between a core 25 and a clad 26. The refractive index of the intermediate layer is smaller than that of the clad. In the refractive index distribution of the core 25, the refractive index is increased as moving from the center axis to the periphery. The laser light guided to the handpiece 15 passes through the optical fiber 9 of the probe 16 and is then emitted from a light emitting face 17. A diseased part is irradiated with the laser light, and an organic hard tissue of the portion is evaporated.

3 Claims, 10 Drawing Sheets

[REFRACTIVE INDEX DISTRIBUTION]

[EMISSION ENERGY PATTERN]

[REFRACTIVE INDEX DISTRIBUTION]

[REFRACTIVE INDEX DISTRIBUTION]

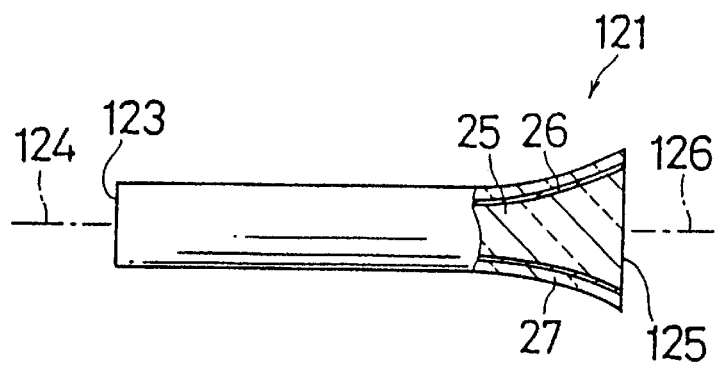
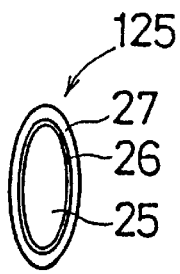
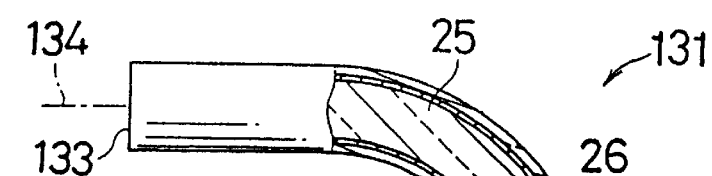
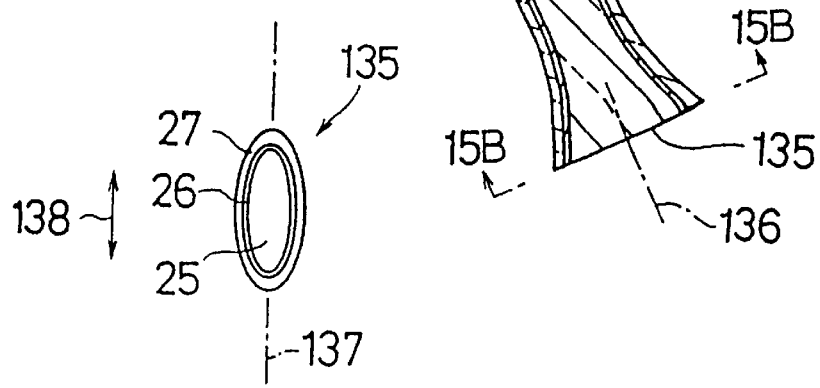

LASER PROBE

BACKGROUND OF THE INVENTION

1. Field of the Invention

The present invention relates to a laser probe which is to be attached to the tip end of a laser handpiece grasped by an operator, and which is made contact with a diseased part of an organic hard tissue such as a bone so as to irradiate the diseased part with laser light.

2. Description of the Related Art

In laser treatment performed in various medical fields, a diseased part is irradiated with laser light in order to carry out vaporization, dissection, coagulation, or hemostatis of an organic soft tissue such as epithelium, musculus, or nervus, and vaporization of an organic hard tissue such as a bone or a tooth bud. For example, an Nd:YAG solid-state laser is used for the purpose of coagulation and hemostatis of the organic soft tissue. A laser light is condensed at the tip end of a conical laser probe made of quartz or sapphire, and the organic soft tissue is irradiated with the laser light to perform treatment such as vaporization, dissection, coagulation, or hemostatis.

As a laser treatment apparatus for treatment of the organic hard tissue, a laser treatment apparatus using an Er:YAG solid-state laser of a wavelength of 2.94 $\mu$m is known. In the apparatus, a laser probe comprising an optical fiber is detachably attached to the tip end of a handpiece, and laser light guided to the handpiece is emitted from the optical fiber of the laser probe. According to the apparatus, treatment is performed by irradiating a diseased part of the organic hard tissue with the laser light so as to vapor the diseased part of the organic hard tissue.

Generally, an optical fiber has a three-layer structure consisting of a core, a clad, and a jacket. The core which is at the center has a refractive index which is higher than that of the clad covering the core. The jacket covers the core and the clad so as to protect them. In accordance with the refractive index distribution in a radial direction of a section of the core, optical fibers are roughly classified into two kinds; a step index optical fiber in which the refractive index is uniform in the refractive index distribution along the direction; and a graded index optical fiber in which the refractive index is gradually reduced as moving from the center of the core to the clad along the direction. In the step index optical fiber, light is propagated with being totally reflected at the interface between the core and the clad. By contrast, in the graded index optical fiber, light is propagated while meandering in the core. A energy density in the irradiation plane of laser light emitted from the light emitting end of such the step index optical fiber is often distributed in accordance with a Gaussian distribution centered at the vicinity of an extension line of the center axis of the optical fiber. In other words, the energy density is higher in the vicinity of an extension of the center axis of the optical fiber, and lower in the vicinity of an extension of the interface between the core and the clad.

In a prior art laser probe used in the above-mentioned laser treatment apparatus for the organic hard tissue, such the step index optical fiber is mainly used. In the laser probe using such the step index optical fiber, when laser light in the form of continuous pulses is emitted for about 5 minutes, the light emitting face is damaged and peeled off, with the result that the vaporization efficiency of the organic hard tissue is lowered. Owing to such a damage or peeling off, the durability of the probe is very low. It is considered that this phenomenon takes place because of the following reason.

In such the laser treatment apparatus, laser light is guided from a laser light source to the body of the handpiece via a guide optical fiber of laser light guiding means, and then enters the optical fiber of the laser probe having a center optical axis which coincides with that of the guide optical fiber. In the guide optical fiber of the laser light guiding means, for example, the laser light is guided in such a manner that the energy level becomes higher as moving toward the center axis of the fiber. The optical fiber of the prior art laser probe to which laser light is guided from such the guide optical fiber has no function of changing the energy distribution of laser light so as to be uniform. When laser light enters as it is the optical fiber of the laser probe, therefore, the energy density of the laser light at the center of the core in the light emitting face of the optical fiber is larger than that in the periphery of the core. This causes the center of the core in the light emitting face to be peeled off or damaged, thereby impairing the durability of the probe.

In the above-described laser treatment apparatus for the organic hard tissue, when the apparatus is to be used for evaporating the organic hard tissue, a laser probe which uses the conventional step optical fiber is mainly used as described above, and the laser probe is attached to the tip end of the handpiece body. The laser probe is made contact with the organic hard tissue, and then the tissue is irradiated with laser light. At this time, organic components of the evaporated organic hard tissue, such as phosphorus, sulfur, and calcium are deposited on the light emitting face of the optical fiber of the laser probe.

When such organic components are deposited on the light emitting face of the optical fiber of the laser probe, heat is generated by laser light absorbed by the deposition and the heat elevates the temperature of the light emitting face. At the same time, the deposition of such organic components causes the melting point of quartz glass ($SiO_2$) which is a principal material of the core, to be lowered. As a result, the light emitting end of the optical fiber of the laser probe is melted at a temperature lower than the melting point of quartz glass, and the light emitting face of the laser probe is peeled off or damaged. This damage proceeds vigorously, particularly in the vicinity of the center axis of the core where the energy density is high. When the organic hard tissue is treated by using such a laser treatment apparatus as described above, furthermore, water is usually supplied in a mist form to a diseased part. Therefore, a thermal stress is produced in the light emitting face of the optical fiber of the laser probe, thereby causing the light emitting face to be further easily peeled off or damaged.

FIG. 17 is a section view showing an optical fiber 1 of a laser probe of the prior art, and more specifically a section view showing the state of the light emitting end of the optical fiber 1 obtained after the laser probe is attached to the above-mentioned laser treatment apparatus of the prior art and the organic hard tissue is continuously irradiated for 20 to 30 seconds with laser light pulses to be vapored. For the sake of convenience in description, a jacket is not illustrated. The optical fiber 1 comprises a core 4 and a clad 5. When the optical fiber 1 is attached to the laser treatment apparatus having the laser probe, and the organic hard tissue is irradiated with continuous pulses of laser light to be vapored, as shown in FIG. 17, for example, the core 4 is cut away after a lapse of 20 to 30 seconds, from the light emitting face 6 before the use and indicated by the two-dot chain line, and the current light emitting face 2 is retracted. When the core 4 is cut away in this manner, the light emitting face 2 has a concave shape or is not flat, so that laser light is scattered by the light emitting face 2, and a gap is formed between the light emitting face and a diseased part. As a result, the vaporization amount of the organic hard tissue per unit time is largely reduced and it is impossible to treat the diseased part.

When continuous pulses are applied via the optical fiber 1 of the laser probe for 20 to 30 seconds so as to vapor the organic hard tissue, for example, the vaporization ability is lowered up to about one-third on average. Therefore, it is difficult to continuously conduct vaporization while uniformly maintaining the vaporization efficiency. In order to maintain the vaporization ability in the laser treatment apparatus, the laser probe comprising the optical fiber 1 must be frequently replaced with a fresh one.

An irradiation apparatus which converts laser light emitted from a laser generator so as to have a laser beam intensity with a Gaussian distribution, into laser light of uniform laser beam intensity, and transmits and applies the converted laser light is disclosed in Japanese Unexamined Patent Publication JP-A 2-297986 (1990). In the irradiation generator, a polygon prism is interposed between the laser device and a guide optical fiber through which laser light is transmitted. When laser light with a Gaussian distribution in both vertical and lateral directions passes through the polygon prism, for example, the intensity distribution of the laser light is uniformized. In the disclosed irradiation apparatus, the strength of laser light emitted from the laser device can be uniformized, but it is difficult to prevent nonuniformity in the laser intensity distribution due to different refractive indices in the optical fiber or the like from occurring in the light emitting end of the optical fiber of the laser probe.

As another prior art technique there is known an ophthalmological laser treatment apparatus which irradiates a diseased part with laser light by means of a laser probe using an optical fiber. The laser treatment apparatus employs pulsate argon laser of a wavelength of 0.514 $\mu$m in order to perform intraocular photocoagulation of a retina. When treatment is performed by laser irradiation from the apparatus, the face to be irradiated can be irradiated with laser light from the light emitting end of the optical fiber of the laser probe, with a uniform energy density. Therefore, excessive or insufficient coagulation hardly occurs.

In the laser treatment apparatus described above, the eye which is an object to be irradiated with laser light is an organic soft tissue. In laser light for intraocular photocoagulation, therefore, a peak value of a pulse (a height of the pulse) which indicates an irradiation energy level is low or about one-thousandth of that of laser light for vaporization of the organic hard tissue. When such low level laser light is emitted via a laser probe comprising the above-described optical fiber of the prior art, the light emitting face of the optical fiber of the laser probe is hardly affected by the laser light because the energy level of the laser light is low, and hence the light emitting face of the optical fiber is not damaged. By contrast, as described above, the durability of a laser probe for emitting high power level laser light which is used for vaporing the organic hard tissue is low because of a damage of the light emitting face of the optical fiber. Consequently, it has been requested to develop a laser probe for organic hard tissues in which the light emitting face of an optical fiber is not damaged and hence the durability is improved.

SUMMARY OF THE INVENTION

It is an object of the invention to provide a laser probe for treating an organic hard tissue and having an optical fiber in which, even in the case of vaporization of the organic hard tissue, a damage of the light emitting face of the optical fiber is suppressed and hence the durability is improved.

The invention provides a laser probe for outputting from an output face of the laser probe, pulse laser light supplied from a laser light source through laser light guiding means and a handpiece, to irradiate an organic hard tissue, the pulse laser light having a wavelength of 1.0 $\mu$m to 5.5 $\mu$m, an output energy of 1 mJ (millijoule) to 2,500 mJ, a pulse width of 1 nS (nanosecond) to 9 mS (milliseconds), and a pulse cycle of 1 pps (pulse per second) to 200 pps, the laser probe being detachably attached to a tip end of the handpiece, and comprising an optical fiber including a core and a clad formed on an outer peripheral face of the core, the optical fiber having a refractive index distribution in which a refractive index of a center portion of the core is lower than a refractive index of a portion of the core surrounding the center portion.

The laser probe of the invention is used while being attached to a handpiece of, for example, a laser treatment apparatus which performs vaporization of the organic hard tissue. In the laser treatment apparatus, laser light generated in the laser light source is guided to the handpiece via the laser light guiding means. The laser probe comprises the optical fiber, and is attached to the tip end of the handpiece. The laser light guided to the handpiece enters the optical fiber of the laser probe to pass through the optical fiber, and is then applied from the light emitting end of the optical fiber to a diseased part of an organic hard tissue which is to be treated. When the organic hard tissue is irradiated with the laser light, water contained in the organic hard tissue is heated to be rapidly evaporated. At this time, organic hard tissue components constituting the organic hard tissue, such as phosphorus, calcium, and sulfur are evaporated together with water.

The evaporated organic hard tissue components are deposited on a light emitting face of the optical fiber from which laser light is emitted. When such hard tissue components are deposited on the light emitting face of the optical fiber, the light emitting face of the optical fiber is clouded and the emittance of laser light is impeded. Furthermore, the deposition of the organic hard tissue components which are organic components causes the melting point of quartz glass ($SiO_2$) constituting the core of the optical fiber, to be lowered.

When laser light passes through a prior art optical fiber and is then emitted from a light emitting face of the optical fiber, for example, the output is caused by the refractive index of the optical fiber to have an energy density distribution with a Gaussian distribution in which the energy density is higher at the center portion of the optical fiber and lower in the periphery. In the light emitting face of the optical fiber, therefore, the center portion has a higher energy density so as to be more easily heated than the periphery. Consequently, the center portion of the light emitting face of the optical fiber on which the organic hard tissue components are deposited is damaged and peeled off to form a concave shape. As a result, the light emitting face of the optical fiber is not a uniform flat face, so that laser light is scattered, thereby lowering the evaporation ability.

The optical fiber disposed in the laser probe for treating the organic hard tissue according to the invention has a configuration in which the outer periphery of the core is covered by the clad. The core has a refractive index distribution in which the refractive index of the center portion is lower than that of a portion surrounding the center portion. When laser light enters such the optical fiber, laser light emitted from the optical fiber has an energy density distribution which is substantially uniform along a radial direction of the core. In the range corresponding to the whole face of the core, therefore, the energy density distribution of laser light which has passed through the optical fiber and is then emitted there from can be uniformized. In the light emitting face of the optical fiber of the laser probe, unlike an optical fiber of the prior art, the energy is not locally concentrated to the vicinity of the center axis. Also when organic hard tissue components are deposited on the light emitting face of the optical fiber, the whole of the light emitting face of the optical fiber generates heat so as to be damaged in a substantially uniform manner. In the case where an organic hard tissue is vapored by using the laser treatment apparatus, even when organic hard tissue components are deposited on the light emitting face of the optical fiber of the laser probe, therefore, the center portion of the light emitting face of the optical fiber is prevented from being damaged and peeled off to form a concave shape. Even when the light emitting face of the optical fiber is damaged, the damage is produced in a substantially uniform manner in the whole of the light emitting face of the optical fiber. Therefore, the reduction of the evaporation ability due to local heat generation in the light emitting face of the optical fiber of the laser probe is prevented from occurring.

In a laser treatment apparatus having a handpiece to which a laser probe comprising a prior art optical fiber is attached, since the damage or peeling off of the light emitting face of the optical fiber of the laser probe proceeds at high rate, the laser probe is worn away at high rate. In order to maintain a predetermined evaporation ability in the laser treatment apparatus using the laser probe, the laser probe must be frequently replaced with a fresh one. In a laser treatment apparatus to which the laser probe of the invention is attached, the concave damage hardly occurs in the light emitting face of the optical fiber of the laser probe. Depending on the level of the energy of laser light, such a damage never occurs in the light emitting face of the optical fiber. As a result, the damage rate of the laser probe is very lower than that in an apparatus of the prior art, and hence the replacement of the laser probe can be conducted at a reduced number.

In a laser treatment apparatus to which the laser probe is attached, even when the number of replacements of the laser probe attached to the laser treatment apparatus is reduced, therefore, the evaporation ability can be maintained. Consequently, the maintenance of the laser treatment apparatus can be easily conducted and the number of consumable parts can be reduced.

When the energy level of laser light is selected to be a level at which the organic hard tissue can be evaporated and the light emitting face of the optical fiber of the laser probe does not excessively generate heat, it is possible to substantially prevent the light emitting face of the optical fiber from being damaged. Such an energy level of laser light is higher than the energy level of laser light of a laser treatment apparatus of the prior art which is used for coagulation of an organic soft tissue such as an eye. Even when the laser probe of a laser treatment apparatus according to the invention is applied to laser light irradiation of such a high energy, the light emitting face of the optical fiber can be prevented from being peeled off or damaged.

In a prior art laser treatment apparatus for treating an organic soft tissue, the durability of a laser probe is not considered. In the laser probe of the invention, in order to prevent the light emitting face of the optical fiber from being peeled off or damaged, the energy distribution in the light emitting face of the optical fiber of the laser probe is substantially uniformized. Laser light from an argon laser which is used for treating an organic soft tissue has a wavelength of 0.514 $\mu$m and a low energy level. Even when the organic hard tissue is irradiated with such laser light, therefore, it is absolutely impossible to evaporate the organic hard tissue. Consequently, the laser device to which the invention is directed is entirely different from that used in a laser treatment apparatus of the prior art in function and effect and also in the kind of emitted laser light.

In the laser treatment apparatus having the handpiece to which the laser probe of the invention is attached, laser light to be emitted has a wavelength of 1.0 $\mu$m to 5.5 $\mu$m and is suitable for vaporization of the organic hard tissue. The laser light has an output energy of 1 mJ to 2,500 mJ. At this energy level, laser light emitted from the laser light source which pulsatively outputs laser light having a pulse width of 1 nS to 9 mS and a pulse cycle of 1 pps to 200 pps can vapor the organic hard tissue, and hardly causes the light emitting face of the optical fiber to be peeled off or damaged. When laser light of such energy level is applied to a diseased part via the laser probe, occurrence of peeling of for damage of the light emitting face of the optical fiber can be made very low or perfectly eliminated. Therefore, the wear rate of the laser probe can be reduced to a very low level or zero.

The optical fiber in the invention is characterized in that:

the optical fiber includes an intermediate layer between the core and the clad, having a refractive index lower than a refractive index of the clad, the refractive index of the clad is lower than the refractive index of the center portion of the core, and the optical fiber has a refractive index distribution in which the refractive index is sharply changed at an interface between the core and the intermediate layer and an interface between the intermediate layer and the clad.

According to the invention, the optical fiber has a three-layer structure in which the intermediate layer exists between the core and the clad. The refractive index of the clad is lower than that of the center portion of the core, and the refractive index of the intermediate layer is lower than that of the clad. In the refractive index distribution of the whole of the optical fiber, the refractive index is sharply changed at the interface between the core and the intermediate layer and that between the intermediate layer and the clad.

As described above, when laser light in a laser treatment apparatus for treatment of the organic hard tissue reaches the light emitting face of the laser probe, the laser light preferably has an energy density distribution which is uniform in a radial direction of a section of the core. When the intermediate layer is interposed between the core and the clad, the energy density of laser light which has passed through the core of the optical fiber is sharply changed at a position corresponding to the interface with respect to the intermediate layer. Therefore, the energy is prevented from leaking into portions corresponding to the intermediate layer and the clad, so that the energy loss of laser light emitted from the light emitting face of the optical fiber is small. Consequently, the energy level of laser light entering the core of the optical fiber can be lowered by the degree corresponding to the reduction amount of the loss.

In the refractive index distribution of the whole of the optical fiber, in this way, the refractive index is gradually lowered in the sequence of the periphery of the core, the center portion of the core, the clad, and the intermediate layer. When the optical fiber is structured in this way, the energy density of laser light passing through the optical fiber is uniformly collected in the range corresponding to the core, thereby preventing the laser light from leaking from the intermediate layer to the outside. Therefore, the energy of laser light entering the core of the optical fiber can be concentrated into the range corresponding to the core, and hence the energy level of the entering laser light can be reduced.

The optical fiber in the invention is characterized in that the core is made of $SiO_2$ to which $GeO_2$ is added in a concentration distribution in which a $GeO_2$ concentration of the peripheral portion of the core is lower than a $GeO_2$ concentration of the center portion of the core, the intermediate layer of the optical fiber is made of $SiO_2$ to which fluorine is added, and the clad of the optical fiber is made of single $SiO_2$.

According to the invention, the optical fiber of the laser probe is made of $SiO_2$ (quartz glass). The refractive index of $SiO_2$ can be easily changed by addition of an additive. The additives which are to be added to the core, and the intermediate layer, and the clad are selected so as to establish the above-mentioned level relationships of refractive indices.

For example, $GeO_2$ which is an additive for increasing the refractive index is added to the core. Fluorine which is an additive for decreasing the refractive index is added to the intermediate layer. The clad remains to be made of single $SiO_2$. As a result, the refractive index is gradually lowered in the sequence of the core, the clad, and the intermediate layer. The additive concentration distribution in the core is formed in such a manner that the concentration of the peripheral portion is lower than that of the center portion. When the additive concentration is changed in accordance with the distance from the center axis, the refractive index can be continuously changed in the core.

The above-mentioned additives are used also in optical fibers which are currently usually used, and hence can be easily obtained. As described above, the optical fiber of the laser probe of the invention is made of $SiO_2$ in which the refractive index is controlled by adding additives that are conventionally used, and hence can be easily realized. When the laser probe comprising the optical fiber realized by such materials is attached to the handpiece of the laser treatment apparatus and then used for evaporation of an organic hard tissue, the peeling off or damage of the light emitting face of the optical fiber can be reduced.

The optical fiber in the invention is characterized in that the core of the optical fiber has a diameter of 0.2 mm to 3.0 mm and the laser light has a wavelength of 2.7 $\mu$m to 3.2 $\mu$m.

According to the invention, since the above-mentioned wavelength range of laser light is included in the range in the vicinity of the maximum value of the light absorption wavelength range of water, laser light satisfying the conditions is particularly suitable for evaporation of an organic hard tissue. When laser light of a wavelength in the range is used, the evaporation efficiency is improved and an organic hard tissue can be rapidly evaporated. Therefore, treatment can be efficiently performed. Since the diameter of the core of the optical fiber is small, a diseased part of a small diameter or a small area can be easily irradiated with laser light. When such laser light enters the core of the optical fiber of the above-mentioned configuration, occurrence of peeling off or damage of the light emitting face of the optical fiber can be made very low or perfectly eliminated.

The optical fiber in the invention is characterized in that a concave portion is formed in a center of the core of the light emitting face.

According to the invention, in the light emitting face of the optical fiber, the center portion of the core is formed into a concave shape. When the laser probe comprising the optical fiber of such a shape is attached to the handpiece of the laser treatment apparatus and then used for evaporation of an organic hard tissue, laser light is regularly scattered to a radially outside portion by the light emitting face of the optical fiber, so that laser light is emitted in a wider range. Furthermore, the organic hard tissue can be evaporated with a substantially uniform depth.

Therefore, laser light is scattered in the light emitting end portion and the organic hard tissue of a wider range can be evaporated. As a result, a range which is irradiated with laser light can be uniformly evaporated.

BRIEF DESCRIPTION OF THE DRAWINGS

Other and further objects, features, and advantages of the invention will be more explicit from the following detailed description taken with reference to the drawings wherein:

FIGS. 14A and 14B are an enlarged partial section view showing an optical fiber 121 of a probe attached to a handpiece of a laser treatment apparatus which is a sixth embodiment of the invention, and an enlarged front view of a light emitting face 125 of the optical fiber, respectively;

FIGS. 15A and 15B are an enlarged partial section view showing an optical fiber 131 of a probe attached to a handpiece of a laser treatment apparatus which is a seventh embodiment of the invention, and an enlarged front view of a light emitting face 135 of the optical fiber, respectively;

DETAILED DESCRIPTION OF THE PREFERRED EMBODIMENTS

Figure 1A:
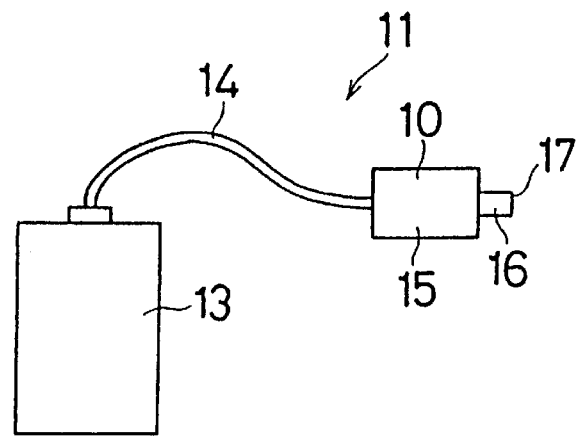
FIG. 1A is a block diagram showing a configuration of a laser treatment apparatus 11 which is a first embodiment of the invention.

Now referring to the drawings, preferred embodiments of the invention are described below.

FIG. 1A is a block diagram showing the configuration of a laser treatment apparatus 11 which is a first embodiment of the invention. The laser treatment apparatus 11 is used for evaporation, dissection, or hemostatis of an organic hard tissue such as a bone. The laser treatment apparatus 11 comprises a laser light source 13, a waveguide 14, and a handpiece 15.

Laser light generated in the laser light source 13 is guided to the handpiece 15 via the waveguide 14. A laser probe 16 is detachably attached to the tip end of the handpiece 15. Namely, the handpiece 15 consists of a handpiece body 10 and the laser probe 16, and the laser probe 16 is mounted on the handpiece body 10. The operator of the laser treatment apparatus (hereinafter, often referred to as merely as "treatment apparatus") 11 makes a light emitting face 17 of the laser probe (hereinafter, often referred to as merely as "probe") 16 attached to the handpiece 15 contact with a diseased part which is to be irradiated with laser light.

The laser light which is guided to the handpiece 15 passes through the laser probe 16 to be emitted from the light emitting face 17, and then impinges on the diseased part. Preferably, water is supplied in a mist form to the surface of the diseased part so that a thin film of water is formed.

Figure 1B:
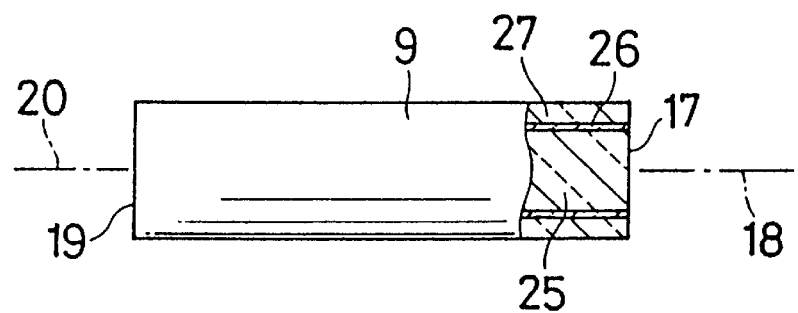
FIG. 1B is a partial section view of a probe 16.

FIG. 1B is a partial section view showing the configuration of an optical fiber 9 of the probe 16, and partially cut away in a virtual plane including the axis. The probe 16 is formed by the optical fiber 9. The optical fiber 9 of the probe 16 is a column-like member in which the section of a light incident face 19 is congruent with that of the light emitting face 17 of the optical fiber 9 that functions as the light emitting face of the probe 16. A center axis 20 of the light incident face 19 of the optical fiber 9 coincides a center axis 18 of the light emitting face 17 of the optical fiber 9.

The organic hard tissue contains a large amount of water. When such an organic hard tissue is irradiated with laser light of a wavelength of 1.0 $\mu$m to 5.5 $\mu$m, the laser light is instantaneously absorbed by the water. The absorbed light energy is converted into thermal oscillation of water molecules, and elevates the temperature of the water, with the result that the water is instantaneously evaporated. This causes the water of the organic hard tissue to be lost, and the organic hard tissue is decomposed and evaporated, with the result that a hole is opened in the organic hard tissue. Through this process, the organic hard tissue is evaporated.

The laser light source 13 outputs pulses of laser light with a predetermined pulse width and a predetermined pulse cycle. For example, the predetermined pulse width of the laser light is 1 nS to 9 ms, and the predetermined pulse cycle of the laser light is 1 pps to 200 pps (pulses per second). The allowable range of the wavelength of the laser light generated by the laser light source 13 is 1.0 $\mu$m to 5.5 $\mu$, and the allowable level of emission energy per pulse of laser light output from the light emitting face 17 of the probe 16 is 1 mJ to 2,500 mJ.

In the case of normal pulses, the pulse width may be in the range of 20 $\mu$S to 30 $\mu$S to 9 mS. When modulation is conducted by an AOQ switch (Acousto-Optical Q-switch), the pulse width may be shortened to 20 nS to 30 nS, and, when modulation is conducted by an EOQ switch (Electro-Optical Q-switch), the pulse width may be shortened to 1 nS.

As described above, in the laser treatment apparatus 11, the pulse width of the laser light which is to be applied to the diseased part is selected from the range of 1 nS to 9 mS. When the diseased part is irradiated with pulsate laser light of a pulse width shorter than 1 nS, for example, the height (peak value) of the pulse must be increased in order to irradiate the diseased part with light of the same energy by one pulse. In this case, the vaporization depth due to one pulse becomes larger, with the result that the diseased part may be evaporated with a depth which is larger than a desired one. When the peak value is higher, the thermal shock caused in the light emitting face 17 of the optical fiber 9 becomes larger. This produces a fear that the durability of the probe 16 is impaired.

By contrast, when the diseased part is irradiated with laser light of a pulse width longer than 9 mS, there is a possibility that the dissection ability in dissection of an organic soft tissue and the hemostatis ability are improved. However, the surface layer of the organic hard tissue which is evaporated as a result of the vaporization of the organic hard tissue may be melted, and the patient which undergoes the treatment may suffer a pain. Since the thermal effect due to one pulse of laser light becomes larger, the thermal denatured layer of the surface of the organic hard tissue may be extended and the diseased part may be thermally affected.

As described above, the pulse cycle of the laser light to be applied to the diseased part is selected so as to be 1 pps to 200 pps. When the pulse cycle is smaller than 1 pps, the cycle is very close to 0 pps, and hence from a viewpoint of working efficiency the laser light irradiation loses the meaning. When the pulse cycle is larger than 200 pps, the vaporization rate on the organic hard tissue is improved, but the size and cost of the laser emitting apparatus are increased. Moreover, the diseased part may be thermally affected in the vaporization of the organic hard tissue.

In view of the circumstances, preferably, the laser treatment apparatus 11 uses laser light having a pulse width of 1 nS to 9 mS and a pulse cycle of 1 to 200 pps.

Figure 2:
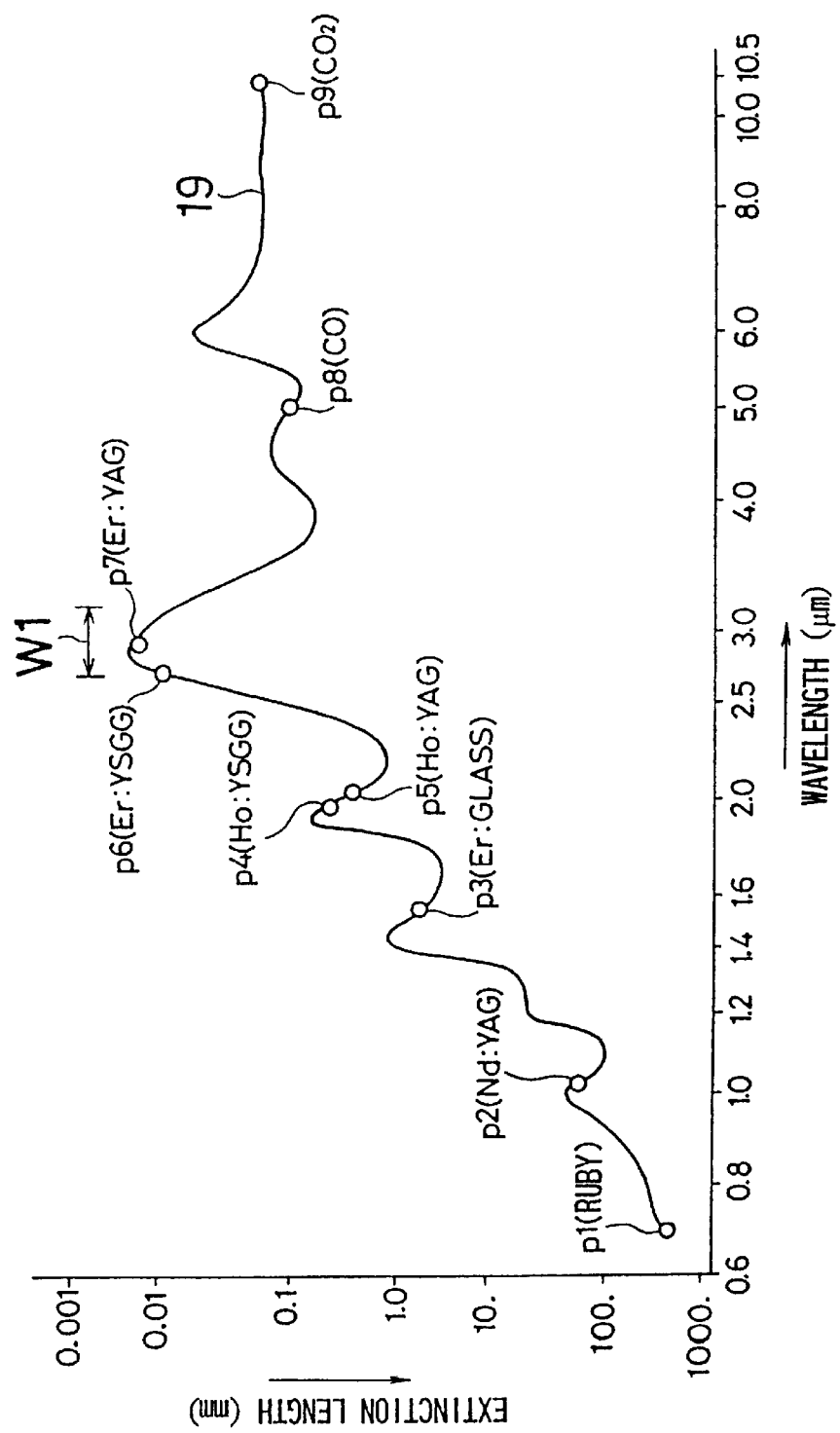
FIG. 2 is a graph showing relationships between the wavelength of laser light and the extinction length.

FIG. 2 is a graph showing a relationship between the wavelength of light and the extinction length. The extinction length is a distance between the surface of water and a position where the energy of laser light entering the surface of water is reduced to ¹/₁₀. The range of an organic hard tissue containing water in the inward direction into which laser light of a wavelength in an allowable wavelength range of 1.0 $\mu$m to 5.5 $\mu$m penetrates is shallower than that into which laser light of a wavelength outside the range penetrates. Therefore, only the surface of a portion of the organic hard tissue which is irradiated with the laser light is supplied with the energy of the laser light and then evaporated. Laser light of a wavelength which is longer than 5.5 $\mu$m has a high absorption efficiency with respect to calcium carbonate and phosphorus constituting the organic hard tissue. When the organic hard tissue is irradiated with such laser light, the organic hard tissue is carbonized. Therefore, it is substantially difficult to use Such laser light in treatment of the organic hard tissue.

An example of the laser light source 13 which outputs laser light of a wavelength in the allowable range of 1.0 $\mu$m to 5.5 $\mu$m is an Er:YAG (erbium; yttrium-aluminum-garnet) solid-state laser. An Er:YAG solid-state laser outputs laser light of a wavelength of 2.94 $\mu$m. Alternatively, an Er:YSGG (erbium: yttrium-scandium-gallium-garnet) solid-state laser which outputs laser light of a wavelength of 2.79 $\mu$m may be used.

The wavelength of laser light emitted from the laser light source is within the wavelength range of 2.7 $\mu$m to 3.2 $\mu$m (the range W1 in FIG. 2) which includes the maximum value of the light absorption wavelength range of water and which is in the allowable wavelength range. When an organic hard tissue is to be vapored by the laser treatment apparatus of the invention, a laser light source which outputs of a wavelength of 2.7 $\mu$m to 3.2 $\mu$m may be used. As a result, efficient treatment can be performed by using the range in which the highest absorption property with respect to water is attained.

Another example of the laser light source 13 which outputs laser light of a wavelength in the allowable range is an Ho:YAG (Holmium: yttrium-aluminum-garnet) solid-state laser. An Ho:YAG solid-state laser outputs laser light of a wavelength of 2.09 $\mu$m. Alternatively, an Ho:YSGG (Holmium: yttrium-scandium-gallium-garnet) solid-state laser which outputs laser light of a wavelength of 2.08 $\mu$m may be used. A Th:YAG (thorium: yttrium-aluminum-garnet) solid-state laser which outputs laser light of a wavelength of 2.01 $\mu$m may be used. A cobalt-vanadium-fluoride solid-state laser which outputs laser light of a wavelength of 1.75 $\mu$m to 2.5 $\mu$m may be used. An Er:GLASS (erbium: glass) solid-state laser which outputs laser light of a wavelength of 1.54 $\mu$m may be used. An Nd:GLASS (neodymium: glass) solid-state laser which outputs laser light of a wavelength of 1.060 $\mu$m maybe used. An Nd:YAG (neodymium: yttrium-aluminum-garnet) solid-state laser which outputs laser light of a wavelength of 1.064 $\mu$m may be used.

A laser light source of a configuration other than the above-mentioned solid-state laser may be used as far as it can output laser light of a wavelength in the allowable range of 1.0 $\mu$m to 5.5 $\mu$m. For example, a gas laser light source such as a CO laser of a wavelength of 5.3 $\mu$m may be used. In the graph of FIG. 2, the void circles p1 to p9 on the solid line 19 respectively indicate wavelengths of laser light output from laser light sources, i.e., a ruby laser, an Nd:YAG solid-state laser, an Er:GLASS solid-state laser, an Ho:YSGG solid-state laser, an Ho:YAG solid state laser, an Er:YSGG solid-state laser, an Er:YAG solid-state laser, a CO laser, and a $CO_2$ laser.

Laser light in the allowable wavelength range is suitable for treatments such as vaporization, dissection, and hemostatis of an organic hard tissue. Particularly, laser light of a wavelength in the range of 2.7 $\mu$m to 3.2 $\mu$m (see W1 in FIG. 2) in the above-mentioned allowable wavelength range has a wavelength within the range which includes the maximum value of the light absorption wavelength range of water. Such laser light has a high absorption efficiency with respect to an organic hard tissue containing water and is suitable particularly for rapidly evaporating an organic hard tissue such as a bone.

The waveguide 14 is realized by, for example, an optical fiber which can guide laser light in the above-mentioned allowable wavelength range with a loss which is as small as possible. An articulated manipulator may be used which consists of hollow members and reflecting mirrors and which allows laser light to pass through the hollow portions of the members while bending the optical path by the reflecting mirrors.

Figure 3:
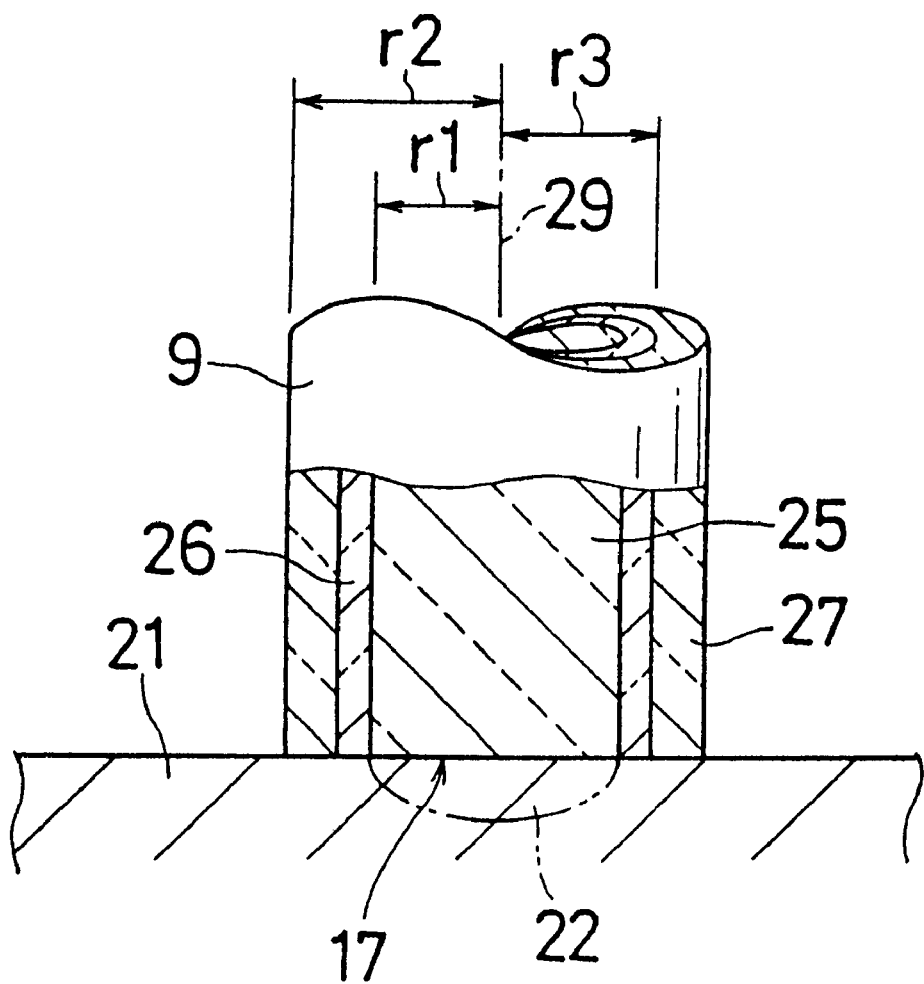
FIG. 3 is a view showing a contact state of an optical fiber 9 of the probe 16 and an organic hard tissue 21 which is to be irradiated with laser light.

FIG. 3 is an enlarged view showing a contact state of the optical fiber 9 constituting the probe 16 and an organic hard tissue 21 which is to be irradiated with laser light. When the organic hard tissue is to be vapored by using the laser treatment apparatus 11, the operator holds the handpiece 15, and makes the light emitting face 17 of the optical fiber 9 constituting the probe 16 contact with the surface of the organic hard tissue 21. As a result, laser light which is generated by the laser light source 13 and guided to the handpiece 15 via the waveguide 14 passes through a core 25 of the optical fiber 9 and then impinges on the surface of the organic hard tissue 21. Thereafter, the laser light penetrates from the surface of the organic hard tissue 21 into the tissue as indicated by the tow-dot chain line 22.

The probe 16 is formed by the optical fiber 9 which causes the energy density of laser light emitted from the light emitting face 17 to be substantially uniform in the range corresponding to the core. As shown in FIG. 3, for example, the optical fiber 9 of the probe 16 comprises the core 25, an intermediate layer 26, and a clad 27.

In the optical fiber 9, the intermediate layer 26 is formed on the outer periphery of the cylindrical core 25, and the clad 27 on the outer periphery of the intermediate layer 26. The core 25, the intermediate layer 26, and the clad 27 are formed concentrically as seen from a virtual plane which is perpendicular to a center axis 29 of the core 25. The refractive index n1 of the material of the core 25 is made larger as the distance from the center axis 29 becomes larger in the core 25. The refractive index n2 of the material of the clad is smaller than the refractive index n1c of the material of the core 25 in the vicinity of the center axis 29. The refractive index n3 of the material of the intermediate layer 26 is smaller than the refractive index n2 of the material of the clad.

The core 25, the intermediate layer 26, and the clad 27 are made of quartz glass ($SiO_2$) containing an additive. The additive is used for adjusting, or increasing or reducing the refractive index of $SiO_2$. For example, additives which can increase the refractive index are $GeO_2$, $TiO_2$, $P_2O_5$, and $Al_2O_3$, and those which can reduce the refractive index are fluorine (F) and $B_2O_3$. As the concentration of such an additive with respect to $SiO_2$ is made higher, the refractive index can be made larger or smaller as compared with that of single $SiO_2$.

Figure 4A:
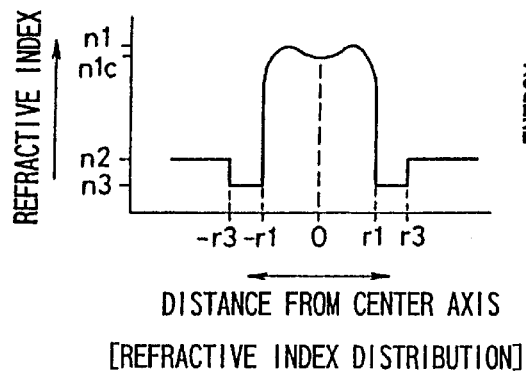
FIG. 4A is a graph showing the refractive index distribution of the optical fiber 9 used in the probe 16 of FIG. 3.

FIG. 4A is a graph showing the refractive index distribution of the optical fiber 9 of FIG. 3 in a radial direction perpendicular to the center axis 29. In the graph, the distance from the center axis 29 of the probe 16 is indicated as the abscissa, and the refractive index of the material at each position as the ordinate. The refractive index distribution is axisymmetric in a section direction about the center axis 29, and changes in the graph so as to be laterally symmetric. With reference to the refractive index n1c on the center axis 29, the refractive index n1 of the core 25 in a circular range centered at the center axis 29 and of a radius r1 is larger as being more distant from the center axis 29, and rapidly reduced at the interface between the core 25 and the intermediate layer 26.

The clad 27 exists outside a circle centered at the center axis 29 and of a radius r3 and inside a circle of a radius r2. The refractive index n2 of the clad 27 which is in this range is smaller than the refractive index n1c of the core 25 on the center axis 29. The intermediate layer 26 exists outside a circle centered at the center axis 29 and of a radius r1 and inside a circle of a radius r3. The refractive index n3 of the intermediate layer 26 which is in this range is smaller than the refractive index n2 of the clad 27. The difference between the refractive index n3 of the intermediate layer 26 and the refractive index n2 of the clad 27 is smaller than that between the refractive index n1c of the core 25 on the center axis 29 and the refractive index n2 of the clad 27.

Figure 4B:
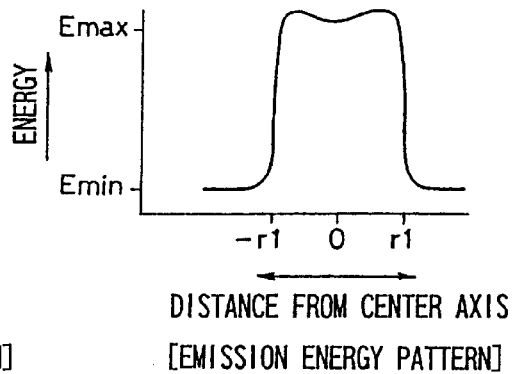
FIG. 4B is a graph showing the energy density distribution of laser light which enters the optical fiber 9 and is then emitted therefrom.

FIG. 4B is a graph showing the energy density distribution of laser light which enters and passes through the optical fiber 9 showing the refractive index distribution of FIG. 4A and is then emitted therefrom. The energy density of the emitted laser light distributes about the center axis 29 of the core 25. Inside the range corresponding to the core 25 or the range in which the distance is larger than −r1 and smaller than +r1, the energy density level is substantially uniform or is the maximum value Emax. Outside the range corresponding to the core 25, the energy density level is the minimum value Emin. The energy density level is rapidly lowered at the portion corresponding to the interface between the core 25 and the intermediate layer 26, and the leakage of the energy is small in amount.

As the material of the core 25 of the optical fiber 9 constituting the probe 16 shown in FIG. 3, $SiO_2$ to which $GeO_2$ is added is selected. As the material of the intermediate layer 26, $SiO_2$ to which fluorine is added is selected. As the material of the clad 27, single $SiO_2$ is selected. The core 25, the intermediate layer 26, and the clad 27 may be made of materials other than those described above, as far as the materials satisfy the above-mentioned level relationships of the refractive indices. For example, $SiO_2$ to which $B_2O_3$ is added may be used as the material of the core 25.

Figure 5A:
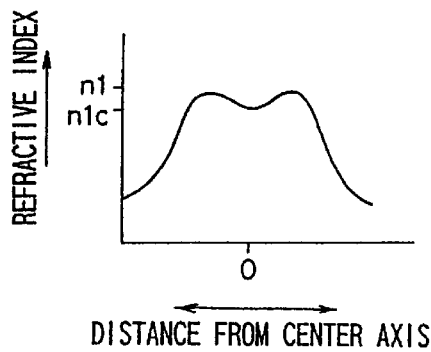
FIG. 5A is a graph showing the refractive index distribution of the transparent base material of the optical fiber 9 of the probe 16 of FIG. 3.
Figure 5B:
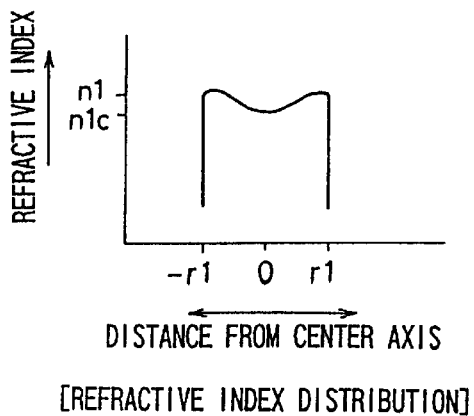
FIG. 5B is a graph showing the refractive index distribution of the base material of the core.

The optical fiber 9 is formed by a fiber base material showing the same refractive index distribution as that of FIG. 4A. For example, the base material of the center core 25 is first formed. The base material of the center core 25 is produced in the following manner. First, a transparent base material showing the refractive index distribution of FIG. 5A is produced by using the VAD (Vapor phase Axial Deposition). The outer periphery of the base material is etched away by a plasma jet. As a result, the base material of the core 25 showing the refractive index distribution of FIG. 5B is produced. For example, the base material of the center core 25 is $SiO_2$ to which GeO is added. In the refractive index distribution of the base material of the core 25, the refractive index is substantially uniform in the base material and sharply changed at an interface between the base material and the external material.

A raw material of the intermediate layer 26 is deposited in a laminated manner on the outer periphery of the thus obtained base material of the core 25, by using, for example, the external CVD (Chemical Vapor Deposition) technique, thereby forming the base material of the Intermediate layer 26. For example, the base material of the intermediate layer 26 is $SiO_2$ to which fluorine is added. The base material of the clad 27 is produced around the outer periphery of the base material of the intermediate layer 26 in the same manner as the base material of the intermediate layer 26. As a result, the fiber base material is formed.

The probe 16 of the invention having the optical fiber 9 of the structure shown in FIG. 3 was attached to the handpiece 15 of the laser treatment apparatus 11 of FIG. 1 in which an Er:YAG solid-state laser is used as the laser light source 13, and the durability of the probe 16 was checked while irradiating an organic hard tissue with a laser light. Hereinafter, the procedure and the results are described in detail.

In this checking operation, the core 25 of the optical fiber 9 in the probe 16 is realized by $SiO_2$ to which $GeO_2$ is added. In the optical fiber 9, moreover, first and second films constituting the jacket are formed on the outer peripheral face of the clad 27. The first film is made of a silicon material. The second film is made of a nylon or Teflon (polytetrafluoroethylene) polymer or a metal such as aluminum, gold, copper etc. The core 25, the intermediate layer 26, and the clad 27 are protected by the jacket formed by the first and second films.

In the checking operation, the probe 16 having the thus configured optical fiber 9 is attached to the tip end of the handpiece 15, and the light emitting face 17 of the fiber is made contact with the surface of the organic hard tissue. Under this state, laser light having predetermined energy per pulse is continuously emitted. The organic hard tissue 21 to be vapored which is used in this experiment is a cattle bone. The continuous irradiation time of laser light is converted from the number of pulses of laser light applied to the organic hard tissue 21 after the start of irradiation. When the repetition frequency is 10 pps (pulses per second), for example, a pulse of laser light having a predetermined pulse width is applied 10 times during one second.

In the checking operation, the laser treatment apparatus 11 having the above-mentioned laser probe 16 of the invention is used, and the organic hard tissue 21 which is moved in a given direction at a predetermined velocity is continuously irradiated with laser light having energy per pulse of 100 mJ and the repetition frequency of 10 pps (hereinafter, such laser light is referred to as merely "laser light of 100 mJ×10 pps"). Therefore, the laser light irradiation position on the organic hard tissue 21 is changed each time when one pulse of laser light is applied, and a new portion of the organic hard tissue 21 is vapored and cut away each time when one pulse of laser light is applied, whereby a vapored portion is formed. When the organic hard tissue 21 is continuously irradiated with the laser light as described above, plural vapored portions are formed on the organic hard tissue 21 in accordance with the temporal movement of the irradiation position.

Figure 6:
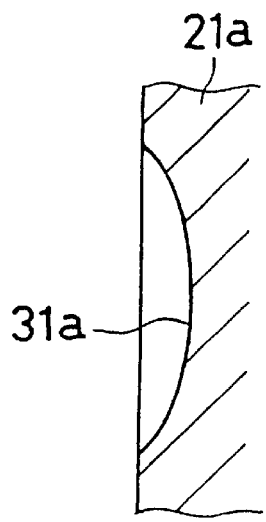
FIG. 6 is an enlarged partial section view of an organic hard tissue 21a which, before continuous irradiation, was irradiated with one pulse of laser light (100 mJ×10 pps) applied via the optical fiber 9 of the probe 16 of the invention in order to check the temporal change of vaporization of the organic hard tissue due to the laser light.
Figure 7:
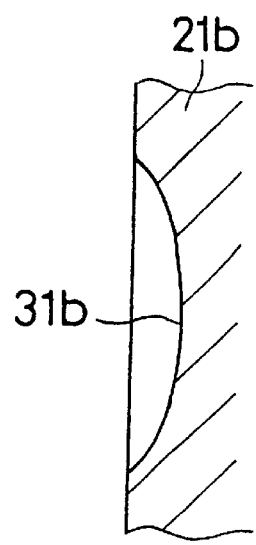
FIG. 7 is an enlarged partial section view of an organic hard tissue 21b which was irradiated with one pulse of laser light of 100 mJ×10 pps by the optical fiber 9 of the probe 16 of the invention which has been used for continuous irradiation of the laser light for 30 minutes, for checking the temporal change of evaporation of the organic hard tissue due to the laser light.

FIG. 6 is an enlarged partial section view of a vapored portion 31a of an organic hard tissue 21a which was formed by, before the organic hard tissue 21 is continuously irradiated with laser light by using the laser treatment apparatus 11 of FIG. 1 to which the probe 16 of FIG. 3 of the invention is attached, irradiating the organic hard tissue 21 with one pulse of laser light in order to check the initial vaporization state of an organic hard tissue due to the energy of the irradiation. FIG. 7 is an enlarged partial section view of an vapored portion 31b of an organic hard tissue 21b which was formed by, after the elapse of 30 minutes from the start of irradiation, irradiation of one pulse of laser light.

The organic hard tissues 21a and 21b shown in FIGS. 6 and 7 will be compared with each other. The organic hard tissue 21a is irradiated with one pulse of laser light by using the probe 16 before the continuous laser light irradiation, and the range which is irradiated with the laser light is vapored in a damaged-ball-like shape, thereby forming the vapored portion 31a of a damaged-ball-like shape. The organic hard tissue 21b is irradiated with one pulse of laser light by using the probe 16 which has been used for continuous laser light irradiation for 30 minutes, and the range which is irradiated with the laser light is vapored in a damaged-ball-like shape, thereby forming the vapored portion 31b of a damaged-ball-like shape. When the two vapored portions 31a and 31b are compared with each other, it will be seen that their shapes, areas, and depths are not substantially changed. Also, it will be seen that the vapored portions 31a and 31b are substantially unchanged in surface roughness. Therefore, the vaporization ability of the treatment apparatus 11 is not changed during the continuous irradiation for 30 minutes.

When the light emitting face 17 of the optical fiber 9 constituting the probe 16 is peeled off or damaged in a concave shape, the vaporization ability of the treatment apparatus 11 is lowered. Even after laser light irradiation is continuously conducted under the above-mentioned conditions for 30 minutes, the vaporization ability remains unchanged. From the above, it will be considered that, when laser irradiation is conducted under the conditions, the light emitting face 17 is not damaged. After the organic hard tissue 21 is irradiated with laser light under the above-mentioned conditions for 30 minutes, the state of the light emitting face 17 of the optical fiber 9 constituting the probe 16 is checked. The state of the light emitting face 17 is substantially equal to that before the use except that soil is deposited in a cloudy form, and no peeling off or damage is observed on the light emitting face 17.

Figure 8:
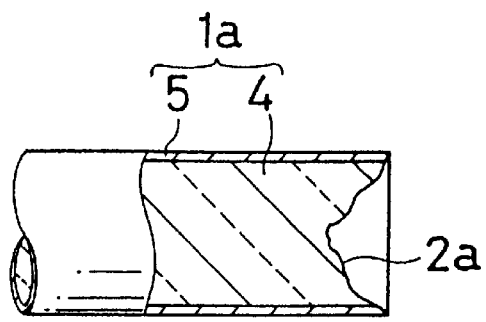
FIG. 8 is an enlarged partial section view of the light emitting end of an optical fiber 1a of a probe of the prior art which was continuously irradiated for 5 minutes with laser light (100 mJ×10 pps) applied via an optical fiber 1 of a probe of the prior art in order to check the temporal change of vaporization of an organic hard tissue due to the laser light.
Figure 17:
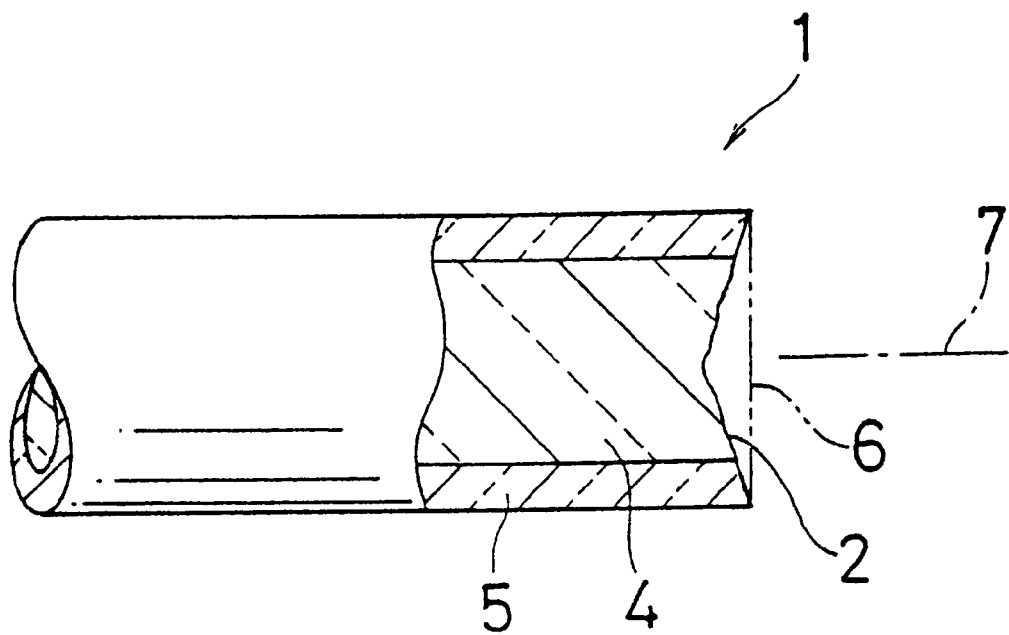
FIG. 17 is an enlarged section view showing an optical fiber 1 of a probe of a laser treatment apparatus of the prior art.

As a comparison of the above-mentioned checking operation, an organic hard tissue which is to be vapored is continuously irradiated for 5 minutes with pulsate laser light of 100 mJ×10 pps emitted from the probe comprising the prior art optical fiber 1 shown in FIG. 17, while moving the organic hard tissue in a given direction at a predetermined velocity. As a result of continuous laser light irradiation under the conditions for 5 minutes, the light emitting face 2a of the optical fiber 1a was damaged in a concave shape as shown in FIG. 8. The damage is deeper as moving toward the center of the core 4 of the optical fiber 1a. At this time, quartz glass (SiO$_2$) was in a completely molten state.

From the above-mentioned results, when, in place of the probe 16 having the optical fiber 9, the probe comprising the prior art optical fiber 1 is attached to the treatment apparatus 11 and irradiation of laser light of 100 mJ×10 pps is conducted, the vaporization ability is lowered to a half or less by continuous irradiation for 5 minutes. Consequently, it will be seen that this configuration cannot be used in actual treatment of an organic hard tissue. When the probe 16 of the invention is used as the probe of the laser treatment apparatus 11, therefore, the reduction of the vaporization ability can be suppressed and the number of replacements of the probe can be reduced as compared with the case where the prior art probe is used in place of the probe 16.

Figure 9:
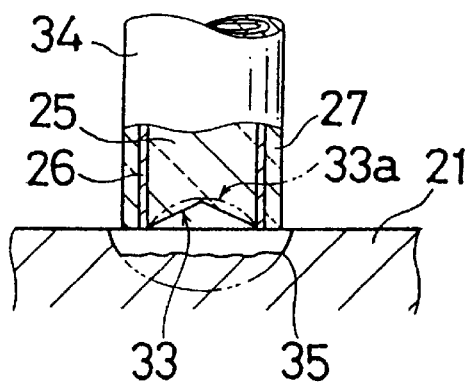
FIG. 9 is an enlarged section view showing the light emitting end of an optical fiber 34 of a probe used in a laser irradiation apparatus which is another example of the first embodiment and in which the bottom face of an evaporation portion has a flat shape.

As another example of the probe 16 of the embodiment, it may be contemplated that, as shown in FIG. 9, the probe comprises an optical fiber 34 having a light emitting face 33 in which the center portion of the core 25 is previously recessed into a concave shape. When, in place of the probe 16 comprising the optical fiber 9, the probe comprising the optical fiber 34 is attached to the treatment apparatus 11 and an organic hard tissue is vapored, emitted laser light is scattered by the light emitting end, and hence the bottom face of the vapored portion of the organic hard tissue 21 has a wide flat shape as indicated by the solid line 35. The light emitting face 33 of the probe comprising the optical fiber 34 may have a conical concave shape as indicated by the solid line, or alternatively have a bowl-like concave shape as indicated by the two-dot chain line 33a.

Figure 10:
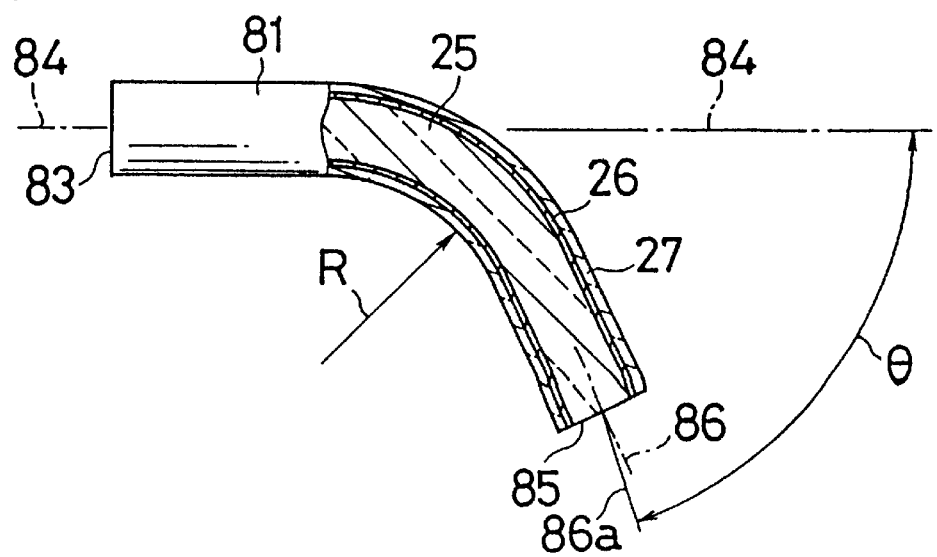
FIG. 10 is an enlarged partial section view showing an optical fiber 81 of a probe attached to a handpiece of a laser treatment apparatus which is a second embodiment of the invention.

FIG. 10 shows an optical fiber 81 used in a probe which is to be attached to the handpiece 15 of the laser treatment apparatus 11 and which is a second embodiment of the invention. FIG. 10 is an enlarged partial section view showing the configuration partially cut away in a virtual plane including the axis. The laser treatment apparatus 11 is configured in the same manner as the laser treatment apparatus 11 of FIG. 1, except the probe comprising the optical fiber 81 of the embodiment. The optical fiber 81 constituting the probe of the embodiment has a configuration similar to that of the optical fiber 9 constituting the probe 16 of the first embodiment. The corresponding components are designated by the same reference numeral, and their detailed description is omitted.

The optical fiber 81 constituting the probe of the embodiment has the same section structure as that of the optical fiber 9 constituting the probe 16 of the first embodiment. The core 25, the intermediate layer 26, and the clad 27 are concentrically arranged in this sequence from the center axis. The optical fiber 81 is a column-like member in which the section is kept to be uniform in shape and size from a light incident face 83 to a light emitting face 85. The optical fiber 81 is curved in the longitudinal direction of the optical fiber 81 and in a virtual plane including the axis. Therefore, the linear center axis 84 of the light incident face 83 and the linear center axis 86 of the light emitting face 85 are connected to each other with being curved in the curved portion R so as to be formed as one curve. Laser light is guided to the light emitting end along the curve or with being curved from an extension line of the center axis 84, and then emitted in a direction which approximately coincides with that of the center axis 86. The energy distribution of the emitted laser light is substantially uniform in a range corresponding to the area of the core 25 in the light emitting face 85.

Preferably, a diseased part which is to be irradiated with laser light is irradiated with laser light in a direction normal to the surface of the part. In the handpiece 15 to which the probe 16 of the first embodiment is attached, the direction of the laser light irradiation coincides with the center axis of the handpiece 15. When the diseased part is in a portion where it is difficult to freely move the handpiece 15, for example, it may be difficult to make the direction of the laser light irradiation coincident with the normal direction of the surface of the diseased part. In this case, when the handpiece 15 to which the probe comprising the optical fiber 81 of the present embodiment is attached is used, the laser light irradiation direction 86a is deviated by an angle θ from the center axis 84 of the light incident face 83 which coincides with that of the handpiece 15, and hence laser light irradiation can be easily conducted in the normal direction of the surface of the diseased part. The handpiece 15 to which the probe comprising the optical fiber 81 is attached is preferably used for irradiating a diseased part in a portion which is difficult to see or is in a small body cavity, with laser light.

Figure 11:
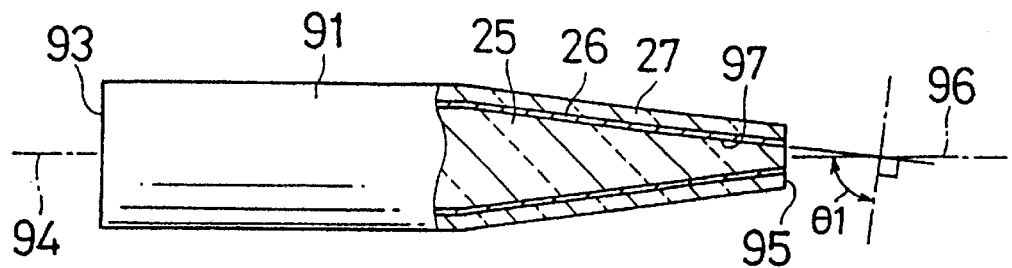
FIG. 11 is an enlarged partial section view showing an optical fiber 91 of a probe attached to a handpiece of a laser treatment apparatus which is a third embodiment of the invention.

FIG. 11 shows an optical fiber 91 used in a probe which is to be attached to the handpiece 15 of the laser treatment apparatus 11 and which is a third embodiment of the invention. FIG. 11 is an enlarged partial section view showing the configuration partially cut away in a virtual plane including the axis. The laser treatment apparatus 11 is configured in the same manner as the laser treatment apparatus 11 of FIG. 1, except the probe comprising the optical fiber 91 of the embodiment. The probe comprising the optical fiber 91 of the embodiment has a configuration similar to that of the probe 16 of the first embodiment The corresponding components are designated by the same reference numeral, and their detailed description is omitted.

The optical fiber 91 used in the probe of the embodiment has the same section structure as that of the optical fiber 9 used in the probe 16 of the first embodiment. The core 25, the intermediate layer 26, and the clad 27 are concentrically arranged in this sequence from the center axis. In the optical fiber 91, the portion from a light incident face 93 to the center portion in the longitudinal direction is realized by a column-like member in which the section is kept to be uniform in shape and size, and the portion from the center portion to the light emitting face 95 is realized by a substantially conic member in which the section shape is kept to be similar but the section size becomes smaller as moving toward the light emitting face 95. The center axis 94 of the light incident face 93 and the center axis 96 of the light emitting face 95 coincide with the same virtual straight line. In this way, the diameter of the optical fiber 91 is gradually reduced as moving from the center portion in the longitudinal direction to the light emitting end. In the optical fiber 91, for example, the portion from the center portion in the longitudinal direction to the light emitting end is formed so that the angle θ1 formed by the normal line of the interface 97 and the center axis 94 is equal to or greater than the critical angle of the optical fiber 91 and the incident light is propagated to the light emitting end with being totally reflected at the interface 97. According to this configuration, the attenuation amount of laser light is reduced.

When laser light which has entered the core 25 from the light incident face 93 of the optical fiber 91 is emitted from the light emitting face 95, the laser light is squeezed and the light density is increased. The energy distribution of the emitted laser light is uniform in a range corresponding to the area of the core 25 in the light emitting face 95. According to this configuration, the energy density of the emitted laser light is increased further uniformly in the vicinity of the extension line of the center axis, and the vaporization efficiency is increased. The irradiation area is smaller than that of the probe 16 of the first embodiment, and hence a fine work can be easily conducted.

Figure 12:
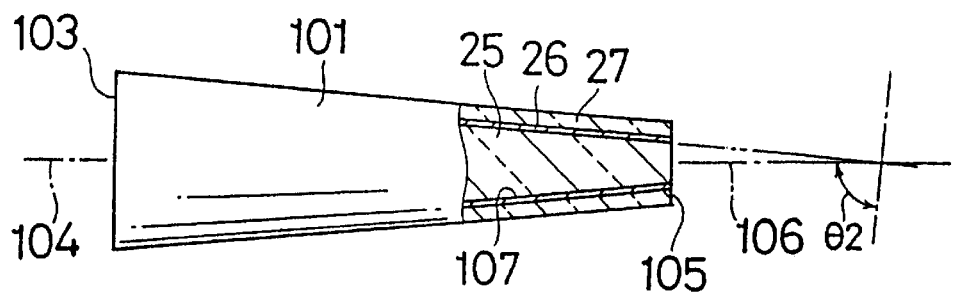
FIG. 12 is an enlarged partial section view showing an optical fiber 101 of a probe attached to a handpiece of a laser treatment apparatus which is a fourth embodiment of the invention.

FIG. 12 shows an optical fiber 101 used in a probe which is to be attached to the handpiece 15 of the laser treatment apparatus 11 and which is a fourth embodiment of the invention. FIG. 12 is an enlarged partial section view showing the configuration partially cut away in a virtual plane including the axis. The laser treatment apparatus 11 is configured in the same manner as the laser treatment apparatus 11 of FIG. 1, except the probe comprising the optical fiber 101 of the embodiment. The optical fiber 101 constituting the probe of the embodiment has a configuration similar to that of the optical fibers 9 and 91 constituting the probes 16 of the first and third embodiments. The corresponding components are designated by the same reference numeral, and their detailed description is omitted.

The optical fiber 101 used in the probe of the embodiment has the same section structure as that of the optical fiber 9 used in the probe 16 of the first embodiment. The core 25, the intermediate layer 26, and the clad 27 are concentrically arranged in this sequence from the center axis. The optical fiber 101 from a light incident face 103 to a light emitting face 105 is realized by a substantially conic member in which the section shape is kept to be similar but the section size becomes smaller as moving toward the light emitting face 105. The center axis 104 of the light incident face 103 and the center axis 106 of the light emitting face 105 coincide with the same virtual straight line. In this way, the diameter of the optical fiber 101 is gradually reduced as moving from the light incident face 103 to the light emitting face 105. In the handpiece 15 comprising the optical fiber 101, the density of laser light emitted from the light emitting face 105 is uniformly increased in the range corresponding to the area of the core 15 of the face, and the vaporization efficiency is increased. The irradiation area is smaller than that of the probe 16 of the first embodiment, and hence a fine work can be easily conducted.

The optical fiber 101 is formed so that the angle θ2 formed by the normal line of the interface 107 and the center axis 104 is equal to or greater than the critical angle of the optical fiber 101 and the incident light is propagated to the light emitting end with being totally reflected at the interface 107. When the length of the optical fiber 101 from the light incident face 103 to the light emitting face 105 is equal to that of the optical fiber 91 of the probe of the third embodiment and the light incident faces 93 and 103 and the light emitting faces 95 and 105 are congruent with each other, the angle θ2 formed by the normal line of the interface 107 of the optical fiber 101 and the center axis 104 is smaller than the angle θ1 formed by the normal line of the interface 97 of the probe 91 and the center axis 94. According to this configuration, the attenuation amount of laser light is smaller than that in the case where the probe 91 of the third embodiment is used.

Figure 13:
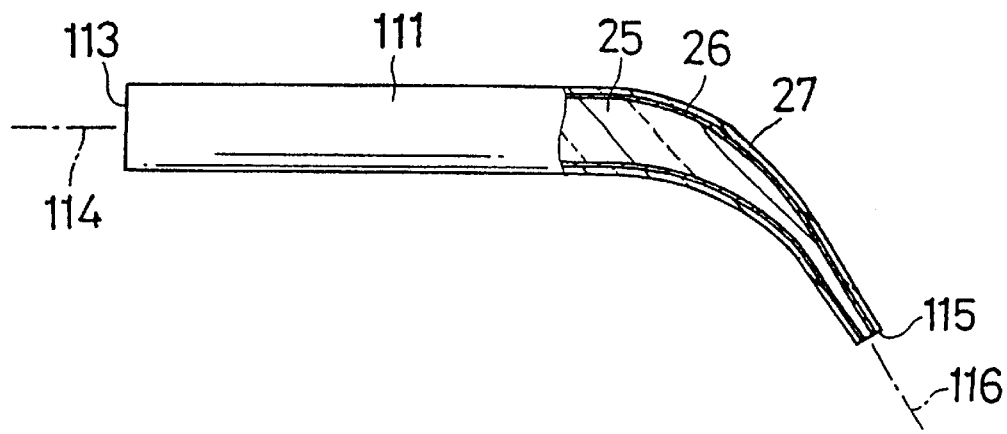
FIG. 13 is an enlarged partial section view showing an optical fiber 111 of a probe attached to a handpiece of a laser treatment apparatus which is a fifth embodiment of the invention.

FIG. 13 shows an optical fiber 111 used in a probe which is to be attached to the handpiece 15 of the laser treatment apparatus 11 and which is a fifth embodiment of the invention. FIG. 13 is an enlarged partial section view showing the configuration partially cut away in a virtual plane including the axis. The laser treatment apparatus 11 is configured in the same manner as the laser treatment apparatus 11 of FIG. 1, except the probe comprising the optical fiber 111 of the embodiment. The optical fiber 111 constituting the probe of the embodiment has a configuration similar to that of the optical fibers 9, 81, and 91 constituting the probes 16 of the first to third embodiments. The corresponding components are designated by the same reference numeral, and their detailed description is omitted.

The optical fiber 111 constituting the probe of the embodiment has the same section structure as that of the optical fiber 9 constituting the probe 16 of the first embodiment, and is made of the same material as that of the optical fiber 9. The core 25, the intermediate layer 26, and the clad 27 are concentrically arranged in this sequence from the center axis. In the optical fiber 111, the portion from a light incident face 113 to the center portion in the longitudinal direction is a column-like member, and the portion from the center portion in the longitudinal direction to the light emitting face 115 is realized by a substantially conic member. The optical fiber 111 is curved in the longitudinal direction and in a virtual plane including the axis of the fiber. The center axis 114 of the light incident face 113 intersects with the center axis 116 of the light emitting face 115 in the virtual plane. Since the optical fiber 111 is curved as described above, laser light is guided to the light emitting end so as to be deviated from the extension line of the center axis 114 of the handpiece 15, and then emitted in the direction along the extension line of the center axis 116. According to this configuration, even a diseased part which is in a narrow portion where it is difficult to freely move the handpiece 15 can be easily irradiated with laser light. The emitted laser light can be squeezed substantially uniformly in a range corresponding to the area of the core of the light emitting face 115, and the vaporization efficiency can be enhanced.

FIG. 14A shows an optical fiber 121 used in a probe which is to be attached to the handpiece 15 of the laser treatment apparatus 11 and which is a sixth embodiment of the invention. FIG. 14A is an enlarged partial section view showing the configuration partially cut away in a virtual plane including the axis. FIG. 14B is an enlarged front view of a light emitting face 125 of the optical fiber 121. The laser treatment apparatus 11 is configured in the same manner as the laser treatment apparatus 11 of FIG. 1, except the probe comprising the optical fiber 121 of the embodiment. The optical fiber 121 of the probe of the embodiment has a configuration similar to that of the optical fiber 9 constituting the probe 16 of the first embodiment. The corresponding components are designated by the same reference numeral, and their detailed description is omitted.

The optical fiber 121 of the embodiment has the same section structure as that of the optical fiber 9 of the probe 16 of the first embodiment, and is made of the same material as that of the optical fiber 9. The core 25, the intermediate layer 26, and the clad 27 are concentrically arranged in this sequence from the center axis. In the optical fiber 121, the portion from a light incident face 123 to the vicinity of the center portion in the longitudinal direction is a column-like member, and the portion from the center portion to the light emitting face 125 is realized by a member having a section shape which is gradually changed from a circular shape to an oval shape as moving from the center portion to the vicinity of the light emitting face 125. The center axis 124 of the light incident face 123 and the center axis 126 of the light emitting face 125 coincide with the same virtual straight line. In this way, the optical fiber 121 has the light incident face 123 and the light emitting face 125 which are different from each other in shape. The energy distribution of emitted laser light is substantially uniform in a range corresponding to the area of the core of the light emitting face 125. According to the handpiece 15 comprising the probe configured by the optical fiber 121, when the probe is moved along the direction of the minor axis of the oval shape of the light emitting face, the laser light irradiation range attained by one scan is larger than that of the handpiece 15 comprising the probe 16 of the first embodiment. Therefore, a diseased piece of a wide area can be efficiently vapored by a smaller number of operations.

FIG. 15A shows an optical fiber 131 used in a probe which is to be attached to the handpiece 15 of the laser treatment apparatus 11 and which is a seventh embodiment of the invention. FIG. 15A is an enlarged partial section view showing the configuration partially cut away in a virtual plane including the axis. FIG. 15B is an enlarged front view of a light emitting face 135 of the optical fiber 131 as seen from A—A. The laser treatment apparatus 11 is configured in the same manner as the laser treatment apparatus 11 of FIG. 1, except the probe comprising the optical fiber 131 of the embodiment. The optical fiber 131 constituting the probe of the embodiment has a configuration similar to that of the optical fibers 9 and 81 constituting the probes 16 of the first and second embodiments. The corresponding components are designated by the same reference numeral, and their detailed description is omitted. The optical fiber 131 is curved in the same manner as the curved optical fiber 81 of FIG. 10, and the light emitting end is formed into an oval shape which vertically elongates.

The optical fiber 131 of the embodiment has the same section structure as that of the optical fiber constituting the probe 16 of the first embodiment, and is made of the same material as that of the optical fiber of the probe 16. The core 25, the intermediate layer 26, and the clad 27 are concentrically arranged in this sequence from the center axis. In the optical fiber 131, the portion from a light incident face 133 to the center portion in the longitudinal direction is a column-like member, and the portion from the center portion in the longitudinal direction to the light emitting face 135 is realized by a member having a section shape which is gradually changed from a circular shape to an oval shape. The optical fiber 131 is curved in the longitudinal direction and in a virtual plane including the axis of the fiber. The center axis 134 of the light incident face 133 intersects with the center axis 136 of the light emitting face 135 in the virtual plane. As shown in FIG. 15B, the light emitting end of the optical fiber 131 is formed so that the light emitting face 135 has a flat oval shape having the major axis 137 which is parallel to the virtual plane. The virtual plane in FIG. 15A is in the sheet on which FIG. 15 is drawn. In FIG. 15B, the direction parallel to the virtual plane is indicated by the arrow 138.

Since the optical fiber 131 is curved in a hoelike shape, laser light is guided to the light emitting end so as to be deviated from the extension line of the linear center axis 134 of the handpiece 15, and then emitted in the direction of the center axis 136 so as to be uniform in a range corresponding to the area of the core of the light emitting face 135. According to this configuration, even In a narrow portion such as a periodontal pocket where it is difficult to freely move the handpiece, a diseased piece of a relatively wide area can be efficiently vapored with scanning the laser light in the direction of the minor axis of the light emitting face of the probe.

Figure 16A:
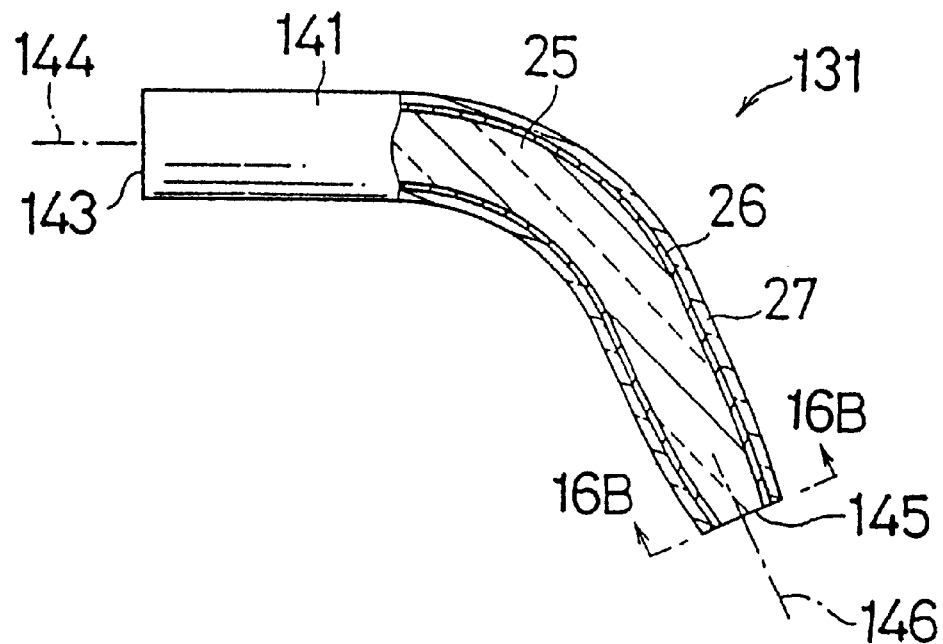
FIGS. 16A and 16B are an enlarged partial section view showing an optical fiber 141 of a probe attached to a handpiece of a laser treatment apparatus which is an eighth embodiment of the invention, and an enlarged front view of a light emitting face 145 of the optical fiber, respectively.
Figure 16B:
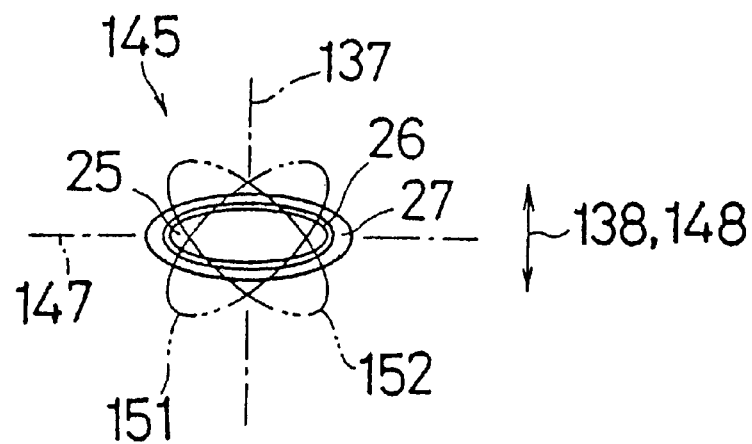

FIG. 16A shows an optical fiber 141 used in a probe which is to be attached to the handpiece 15 of the laser treatment apparatus 11 and which is an eighth embodiment of the invention. FIG. 16A is an enlarged partial section view showing the configuration partially cut away in a virtual plane including the axis. FIG. 16B is an front view of a light emitting face 145 of the optical fiber 141 as seen from B—B. The laser treatment apparatus 11 is configured in the same manner as the laser treatment apparatus 11 of FIG. 1, except the probe comprising the optical fiber 141 of the embodiment. The optical fiber 141 of the probe of the embodiment has a configuration similar to that of the optical fibers 9 and 131 of the probes 16 of the first and seventh embodiments. The corresponding components are designated by the same reference numeral, and their detailed description is omitted. The optical fiber 141 is curved in the same manner as the curved optical fiber 131 of FIG. 15, and the light emitting end is formed into a wide oval shape which laterally elongates.

The optical fiber 141 of the embodiment has the same section structure as that of the optical fiber 9 of the probe 16 of the first embodiment, and is made of the same material as that of the optical fiber. The core 25, the intermediate layer 26, and the clad 27 are concentrically arranged in this sequence from the center axis. In the optical fiber 141, the portion from a light incident face 143 to the center portion in the longitudinal direction is a column-like member, and the portion from the center portion in the longitudinal direction to the light emitting face 145 is realized by a member having a section shape which is gradually changed from a circular shape to an oval shape. The optical fiber 141 is curved in the longitudinal direction and in a virtual plane including the axis of the fiber. The center axis 144 of the light incident face 143 intersects with the center axis 146 of the light emitting face 145 in the virtual plane. As shown in FIG. 16B, the light emitting end of the optical fiber 141 is formed so that the light emitting face 145 has a flat oval shape laterally elongating and having the major axis 147 which is perpendicular to the virtual plane. The virtual plane in FIG. 16A is identical with that of the seventh embodiment. In FIG. 16B, the direction parallel to the virtual plane is indicated by the arrow 148.

Since the optical fiber 141 is curved in this way, laser light is guided to the light emitting end so as to be deviated from the extension line of the linear center axis 144 of the handpiece, and then emitted so as to be substantially uniform in a range corresponding to the area of the core of the light emitting face 145. According to this configuration, even in a narrow portion such as a molar where it is difficult to freely move the handpiece 15, a diseased piece of a relatively wide area can be efficiently vapored by one operation with scanning the laser light in the direction of the minor axis of the light emitting face of the probe.

Another example of the optical fibers 131 and 141 of the probes of the seventh and eighth embodiments is an optical fiber which is curved in the longitudinal direction and has a light emitting face of an oval shape. In the optical fiber, the major axis of the oval of the light emitting face intersects with a virtual plane including the axis of the curved optical fiver. The light emitting end of the optical fiber is formed in the following manner. When the light emitting face is seen along the normal line of the face, as shown in FIG. 16B, the major axis of the light emitting face of the probe intersects with the virtual plane at an angle which is between the angles respectively formed by the major axes 137 and 147 of the light emitting faces 135 and 145 of the optical fibers 131 and 141 and the virtual plane. The light emitting face may have an oval shape in which the major axis indicated by the two-dot chain line 151 is upward slant to the right, or alternatively that in which the major axis indicated by the two-dot chain line 152 is upward slant to the left. The angle formed by the major axis of the light emitting face and the virtual plane may have any value other than 0 deg. and 90 deg.

The probes used in the laser treatment apparatuses 11 of the first to eighth embodiments are configured by an optical fiber in which the core has a diameter of, for example, 0.2 mm to 3.0 mm. Among the embodiments, in the probes used in the apparatuses of the fourth and sixth to eighth embodiments, an optical fiber in which the core diameter in the light incident face is as described above or 0.2 mm to 3.0 mm is used.

When an optical fiber of a core diameter which is smaller than 0.2 mm is used in a probe, laser light can be applied only to a diseased part which has a small diameter or a small area. When an optical fiber of a core diameter which is larger than 3.0 mm is used in a probe, the laser emitting apparatus must be increased in size and hence the production cost of the apparatus is increased. In view of the circumstances, it is preferable to use an optical fiber of a diameter of 0.2 mm to 3.0 mm, in a probe.

In the laser treatment apparatus, as described above, it is preferable to set the energy level of laser light in the light emitting face of the optical fiber of the probe to be in the range of 1 mJ to 2,500 mJ. When laser light has an energy level of 5 mJ to 2,500 mJ, for example, the energy of the laser light is sufficient for a laser treatment apparatus in which an optical fiber of a core diameter of 0.2 mm to 3.0 mm is used as a probe, to vapor an organic hard tissue. When laser light of an energy level which is greater than 2,500 mJ is used for vaporization of an organic hard tissue, the tissue is more largely damaged as compared with the case where laser light of an energy level of 2,500 mJ is used. When laser light of an energy level which is not greater than 1 mJ is used, energy sufficient for evaporating an organic hard tissue cannot be obtained.

The optical fibers 9, 81, 91, 111, 121, 131, and 141 of the probes of the first, second, and fourth to eight embodiments are identical with each other in the shape of the vicinity of the light incidence face, and different from each other only in the shape of the vicinity of the light emitting face. Therefore, the optical fibers are interchangeable in accordance with the shape of the light emitting face. When the probes have the same diameter of the light incidence face of the optical fiber, attachment members for attaching the probes to the handpiece 15 can be structured in the same manner. As a result, these probes can be attached to the handpiece 15 of the identical laser treatment apparatus 11. The optical fibers used in the laser treatment apparatuses 11 of the embodiments may be configured as a noncontact type probe. Furthermore, the optical fibers 9, 81, 91, 111, 121, 131, and 141 may be an optical fiber in which the intermediate layer 26 is not formed, as far as the energy level can be made substantially uniform. In the optical fibers 81, 91, 111, 121, 131, and 141 of the second to eighth embodiments, the light emitting face may be formed into a concave shape in which the center of the core is cut away.

The laser treatment apparatuses in the embodiments may be used for evaporating an organic hard tissue other than a bone, such as a tooth bud, or a cartilage. When the wavelength and energy of laser light are suitably changed, the laser treatment apparatuses may be used for performing dissection, vaporization, or hemostatis of an organic soft tissue.

The invention may be embodied in other specific forms without departing from the, spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A laser probe for organic hard issue, detachably attached to a tip end of a handpiece, for guiding laser light emitted from a laser light source to the handpiece by laser light guiding means, the laser probe comprising an optical fiber having a core and a clad formed on an outer peripheral face of the core, and wherein:

the optical fiber has a refractive index distribution in which a refractive index n1c of a center portion of the core is lower than a refractive index n1 of a portion of the core surrounding the center portion, an intermediate layer is formed between the core and the clad, the refractive index n3 of the intermediate layer is lower than the refractive index n2 of the clad, the refractive index n2 of the clad is lower than the refractive index n1c of the center portion of the core, the optical fiber has a refractive index distribution in which the refractive index is sharply changed at an interface between the core and the intermediate layer and an interface between the intermediate layer and the clad, the core of the optical fiber has a diameter of 0.2 mm to 3.0 mm, the laser light has a wavelength of 1.0 $\mu$m to 5.5 $\mu$m, an output energy of 1 mJ to 2,500 mJ, a pulse width of 1 ns to 9 ms, and a pulse cycle of 1 pps to 200 pps, the core of the optical fiber is made of $SiO_2$ to which an additive selected from the group consisting of $GeO_2$, $TiO_2$, $P_2O_5$ and $Al_2O_2$ is added in a concentration distribution in which the additive concentration of a peripheral portion of the core is lower than the additive concentration of the center portion of the core, the intermediate layer of the optical fiber is made of $SiO_2$ to which one selected from the group consisting of $B_2O_5$ and fluorine is added, and the clad of the optical fiber is made of single $SiO_2$.

2. A laser probe for an organic hard tissue, detachably attached to a tip end of a handpiece, for guiding laser light emitted from a laser light source to the handpiece by laser light guiding means, the laser probe comprising an optical fiber having a core and a clad formed on an outer peripheral face of the core, characterized in that the optical fiber has a refractive index distribution in which a refractive index of a center portion of the core is lower than a refractive index of a portion of the core surrounding the center portion, an intermediate layer is provided between the core and the clad, the laser light has a wavelength of 1.0 $\mu$m to 5.5 $\mu$m, an output energy of 1 mJ to 2,500 mJ, a pulse width of 1 ns to 9 ms, and a pulse cycle of 1 pps to 200 pps, the refractive index of the intermediate layer is lower than the refractive index of the clad, the refractive index of the clad is lower than the refractive index of the center portion of the core, the optical fiber has a refractive index distribution in which the refractive index is sharply changed at an interface between the core and the intermediate layer and an interface between the intermediate layer and the clad, the core of the optical fiber is made of $SiO_2$ to which $GeO_2$ is added in a concentration distribution in which a $GeO_2$ concentration of a peripheral portion of the core is lower than a $GeO_2$ concentration of the center portion of the core, the intermediate layer of the optical fiber is made of $SiO_2$ to which fluorine is added, and the clad of the optical fiber is made of single $SiO_2$.

3. A method for treating an organic hard tissue by using the laser probe according to any of claims 1 to 2.

* * * * *